United States Patent [19]
Meyer

[11] Patent Number: 5,587,540
[45] Date of Patent: Dec. 24, 1996

[54] SOIL SAMPLING DEVICE WITH LATCH ASSEMBLY HAVING A VARIABLE CIRCUMFERENTIAL SHAPE

[76] Inventor: Robert D. Meyer, 13501 Witcher NE., Albuquerque, N.M. 87112

[21] Appl. No.: 491,281

[22] Filed: Jun. 16, 1995

Related U.S. Application Data

[63] Continuation of Ser. No. 189,957, Feb. 1, 1994, abandoned.

[51] Int. Cl.⁶ ..................................................... G01N 1/08
[52] U.S. Cl. ........................................ 73/864.44; 175/20
[58] Field of Search ........................... 73/864.44, 864.45; 175/20, 58, 304, 306; 172/21, 22; 111/7.1

[56] References Cited

U.S. PATENT DOCUMENTS

| | | | |
|---|---|---|---|
| 1,027,246 | 5/1912 | Granville | 73/864.44 |
| 2,709,368 | 5/1955 | Wolpert | 73/864.45 |
| 3,367,188 | 2/1968 | Robinson | 73/864.44 |
| 3,704,627 | 12/1972 | Beaudoux | 73/864.45 |
| 3,978,733 | 9/1976 | Avot | 73/864.45 |
| 4,329,882 | 5/1982 | Kaup | 73/864.44 |
| 4,558,749 | 12/1985 | Fulkerson | 175/58 |
| 4,633,957 | 1/1987 | Prost | 172/22 |
| 5,076,392 | 12/1991 | Koenig | 181/106 |
| 5,125,266 | 6/1992 | Ingram et al. | 73/84 |
| 5,127,261 | 7/1992 | Ingram et al. | 73/84 |
| 5,211,249 | 5/1993 | Richter et al. | 175/20 |

*Primary Examiner*—Hezron E. Williams
*Assistant Examiner*—Nashmiya N. Ashraf
*Attorney, Agent, or Firm*—Timothy D. Stanley; Andrew A. Abeyta

[57] ABSTRACT

The invention relates to an improved sampler which can be operated in any orientation. The design features a positive gripping of the operating rod in a manner to reduce point loads so as to reduce any possibility of jamming of the rod on a retraction stroke until such time as it is positively retained in the fully withdrawn position. In the preferred embodiment, a pair of mating cylindrical latch pieces, held together by a circumferential spring, are used for positive actuation. The inner rod has an angular cut-out which provides the base for the latch when aligned with the latch. A release fixture can be used to free the latch from the cone rod after actuation. The latches are formed in such a manner as they may support themselves within the housing of the sampler until they engage the operating rod.

13 Claims, 4 Drawing Sheets

(SAMPLER ASSEMBLY)

5,587,540

SOIL SAMPLING DEVICE WITH LATCH ASSEMBLY HAVING A VARIABLE CIRCUMFERENTIAL SHAPE

The United States Government has rights in this invention pursuant to Contract No. DE-AC04-76DP00789 between the Department of Energy and American Telephone and Telegraph Company.

This a continuation of application(s) Ser. No. 08/189,957 filed Feb. 1, 1994 now abandoned.

FILED OF THE INVENTION

The field of this invention relates to soil samplers which are used by engineers and technicians to retrieve subsurface soil samples for a variety of reasons.

BACKGROUND OF THE INVENTION

Soil samplers such as cone penetrometers have been used throughout the world by engineers to measure soil properties. Part of the testing regime utilizes soil sampling to help determine mechanical properties at various depths and locations. This data is used for many types of pre- and post-construction evaluation. Other uses for sampling are in the environmental area for monitoring and remediation. Soil sampling is a key diagnostic technology used to demonstrate compliance with the environmental laws.

Many samples, due to the nature of the field conditions, have to be taken in a horizontal position. This would include samples underneath existing structures, such as tanks or other industrial equipment or buildings.

Prior art samplers, such as that shown in FIG. 1 of this application, used a ball and detent latch system, which used gravity to set steel balls in a grooved shaft. The principle of operation was that the balls were to lock the shaft in position to allow the sampler to be pushed forward to obtain a core soil sample. This type of sampler was designed to be pushed vertically into the ground, with the center rod in the forward position. The rod would then be retracted when the sampler reached the target, causing the steel balls to lock and enable the body to be pushed forward to collect the sample. This prior art design had several operating drawbacks, such as premature lock-up, incomplete latching, as well as not being able to operate in a position that was significantly off the vertical position. The problem with the prior design was that retraction of the central shaft was not always a uniform movement and could include some forward motion during the retraction step. With the design as shown in FIG. 1, any forward motion, even to a slight degree, during the retraction step could jam the balls, causing the balls to break or to break the exterior housing or the central shaft when the balls jammed in the tapered housing in which they were stored. Sometimes the balls would not fully latch into the groove, which would cause problems in obtaining the sample, such as sample loss prior to withdrawal of the sampler. The mislatching was primarily due to radial point loads on the latching piece body transmitted through the balls, which caused failure of the body and damage to the cone rod surface.

To address these shortcomings of the prior design, the apparatus and method of the present invention were developed to provide a distributed load-bearing surface with forces preferably in the axial direction. The layout of components is such that positive latching occurs in any orientation. The present invention allows back and forth movement of the rod up until the point of latching without damage to any of the parts. The new design can be accomplished within the dimensions of the old design while retaining its mechanical strength features. Apart from the prior design as shown in FIG. 1, other designs of samplers have been used in the past, as indicated in U.S. Pat. Nos. 5,125,266 and 5,127,261. In this design the sample tube extends out of a housing and into the formation in order to grab the sample.

SUMMARY OF THE INVENTION

The invention relates to an improved sampler which can be operated in any orientation. The design features a positive gripping of the operating rod in a manner to reduce point loads so as to reduce any possibility of jamming of the rod on a retraction stroke until such time as it is positively retained in the fully withdrawn position. In the preferred embodiment, a pair of mating cylindrical latch pieces, held together by a circumferential spring, are used for positive actuation. The inner rod has an angular cut-out which provides the base for the latch when aligned with the latch. A release fixture can be used to free the latch from the cone rod after actuation. The latches are formed in such a manner as they may support themselves within the housing of the sampler until they engage the operating rod.

DETAIL DESCRIPTION OF THE DRAWINGS

DETAILED DESCRIPTION OF THE PREFERRED EMBODIMENT

Figure 1:
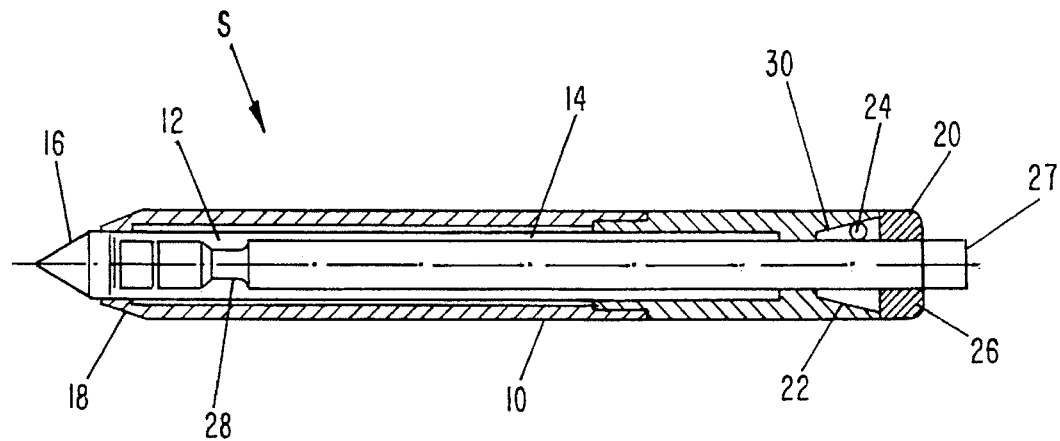
FIG. 1 is a sectional view of a prior art design sampler.

The prior art sampler S is illustrated in FIG. 1. It has a housing 10 around a central bore 12, within which cone rod 14 is reciprocally movable. Cone rod 14 has a tip 16 which conforms to the profile of the leading edge 18 of housing 10. At the upper end 20 of housing 10 is a conical cavity 22 which holds a plurality of latching balls 24. A closure 26 secures the latching balls 24 within conical cavity 22. The rod 14 has a tapered segment 28 adjacent the tip 16. In use, the sampler S of the prior art shown in FIG. 1 is inserted into the ground in a vertical position. The cone rod 14 is retracted until the latching balls 24 are aligned with groove 28. Experience has shown that when the sampler of FIG. 1 is aligned in a position other than vertical, the latching balls 24 frequently jam up against the outer surface of the cone rod 14. These balls at that time will also exert a point load on tapered surface 30. The stress concentration from the point loads in the past has resulted in jamming of the cone rod 14 within the housing 10. The surface of cone rod 14 has been abraded due to the jamming of latching balls 24. Additionally, the upper end 20 of the housing 10 has also broken in the area of tapered surface 30. These problems have arisen for a variety of reasons. One of these reasons is that in normal operation when the cone rod 14 is retracted, the motion is not smooth and unidirectional. Instead, during the retracting step, the cone rod 14 may be temporarily advanced after it has been partially retracted. This type of action has resulted in jamming of the latching balls 24 against tapered surface 30, causing the damage previously described. The latching process itself is incomplete when the sampler of FIG. 1 is oriented in position other than nearly vertical. When oriented in other alignments, the tendency of latching balls 24 to jam against tapered surface 30 is accelerated and failure occurs shortly thereafter. Mislatch can occur anytime that the cone rod is retracted for insufficient distance to set the balls in the detent. This happens frequently during advance of the sampler to the target zone. Many times the bore is preformed, which is the case in a directionally steered bore typical in environmental applications. There are times when the push rods may have to be retracted for an inch or two for any number of operational reasons during these operations.

Figure 2:
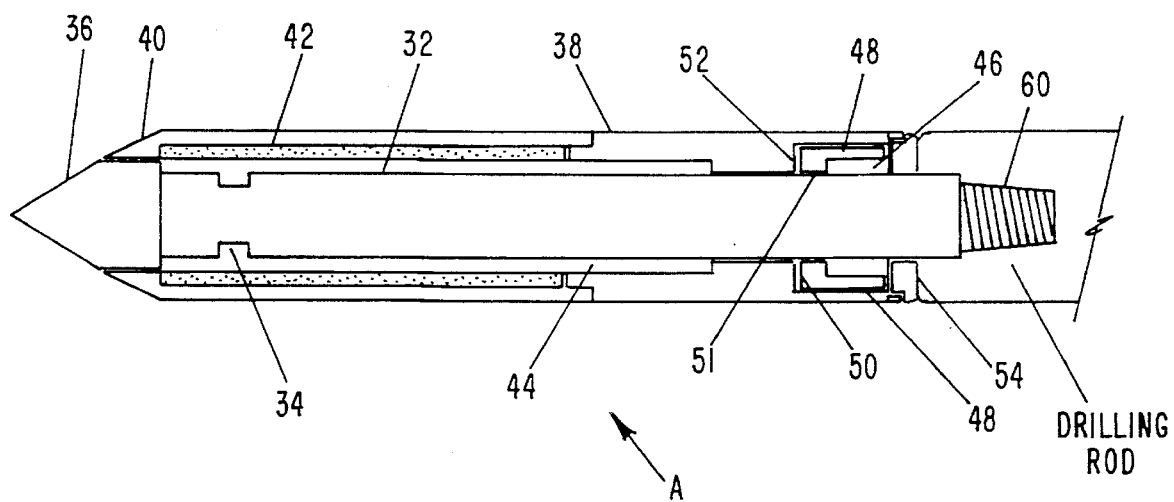
FIG. 2 is a sectional elevational view of the apparatus of the present invention.
Figure 3:
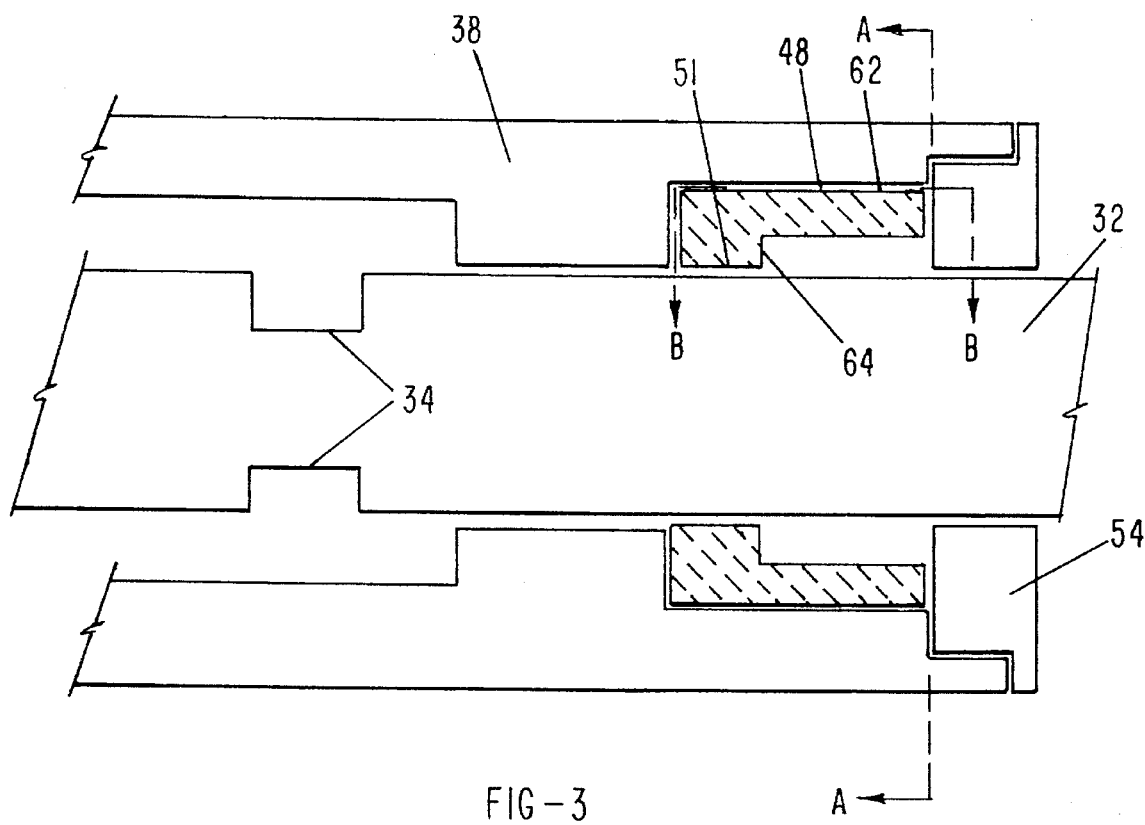
FIG. 3 is a detail of the latch installation as the operating rod comes close to the point of latching.
Figure 4:
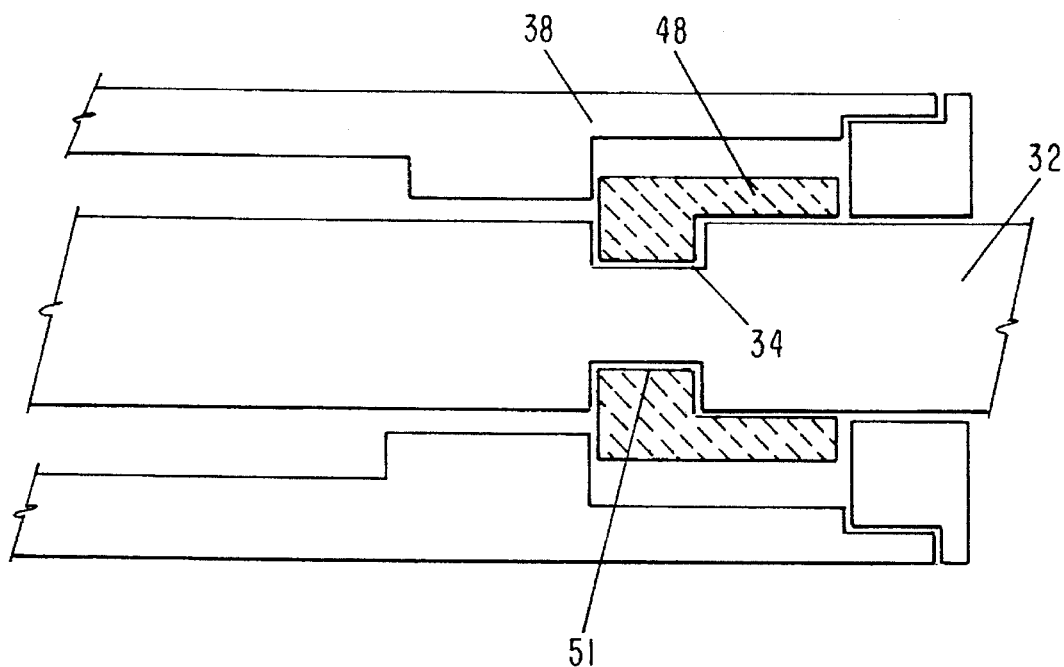
FIG. 4 is the view of FIG. 3 with the rod retracted a sufficient amount to allow the latches to engage the groove.
Figure 5A:
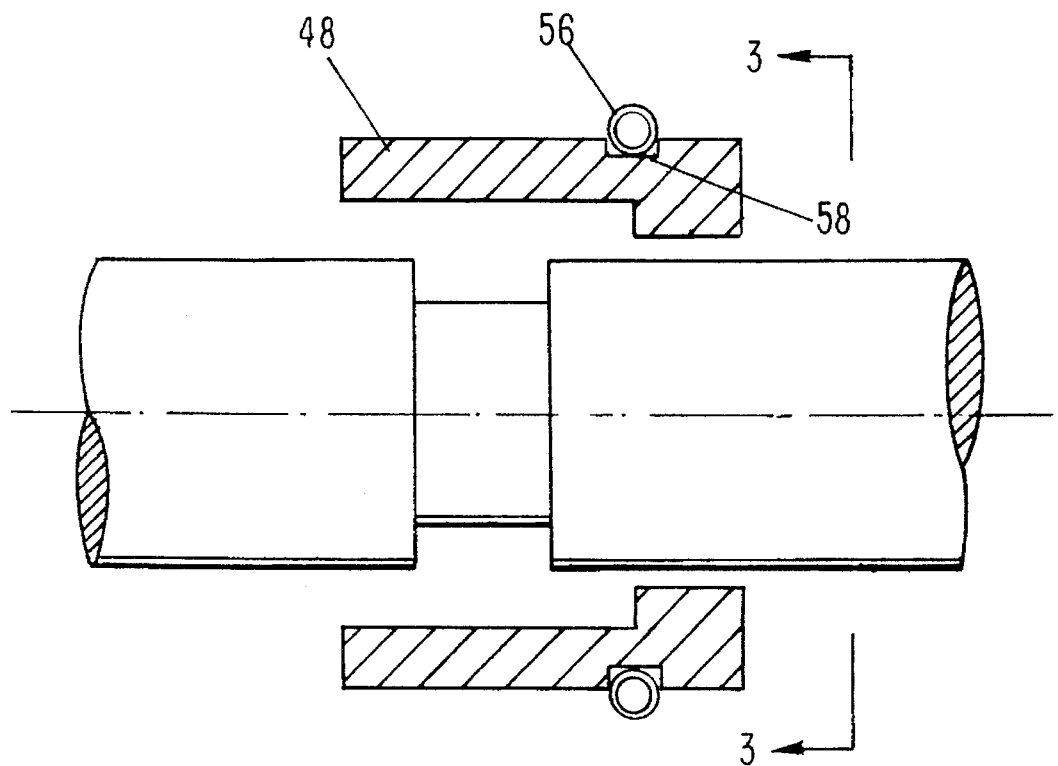
FIGS. 5a and 5b are sectional part assembly views showing the circular spring on the exterior of the movable latches.
Figure 5B:
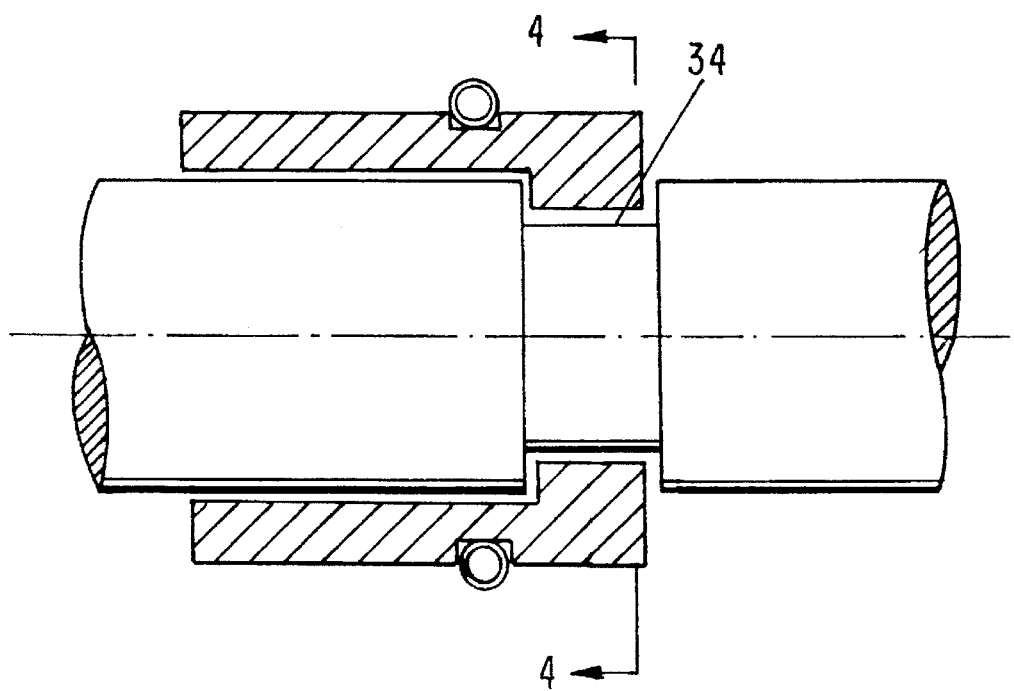
Figure 6A:
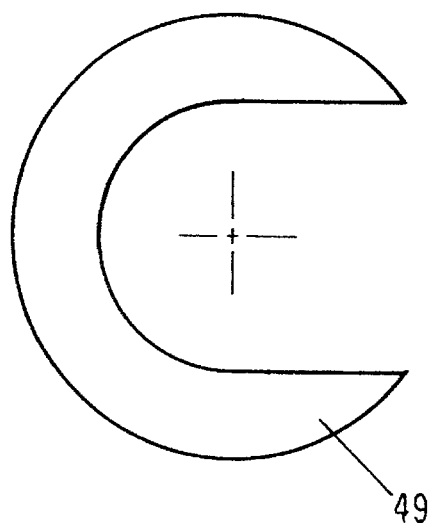
FIG. 6A is a top view of the release tool.
Figure 6B:
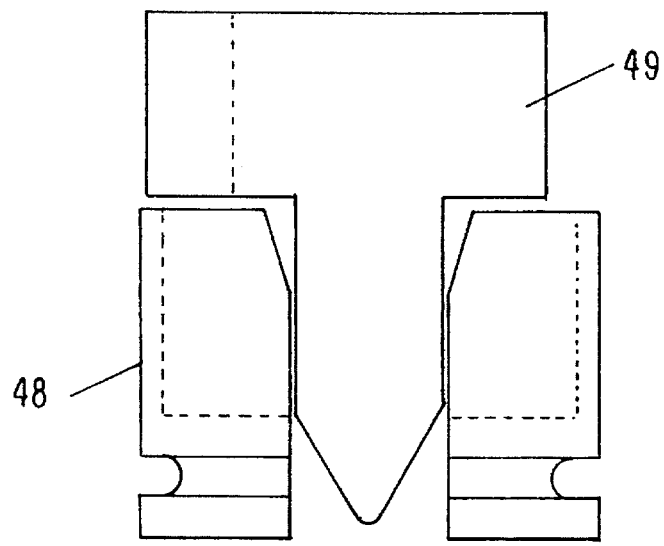
FIG. 6B is an elevational view of the release tool shown spreading the latches apart.
Figure 6C:
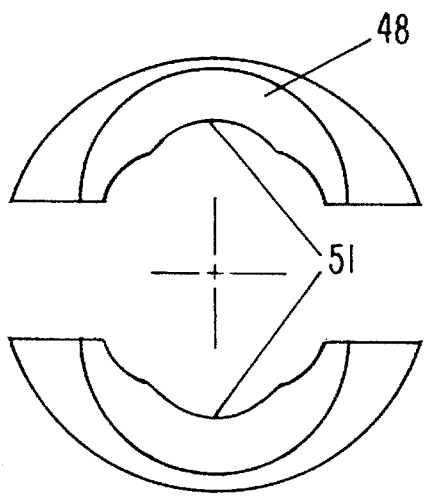
FIG. 6C is a top cutaway view of the latches taken along line A—A depicted in FIG. 3.
Figure 6D:
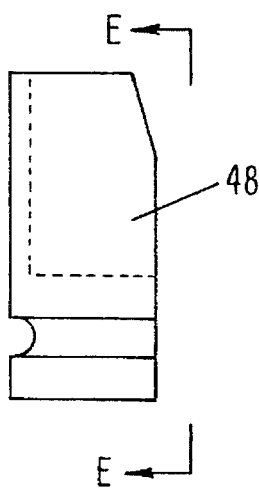
FIG. 6D is a view of the latches taken along line B—B depicted in FIG. 3.
Figure 6E:
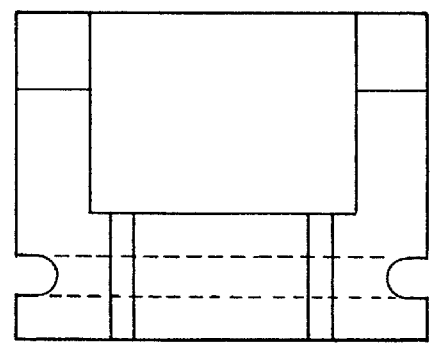
FIG. 6E is another view of the latches taken along line E—E as depicted in FIG. 6D.

The apparatus A of the present invention is illustrated in FIGS. 2–5. As shown in FIG. 2, an operating rod 32 is formed having a groove 34 adjacent its tapered tip 36. The housing 38 of the apparatus A circumscribes the operating rod 32 and has a tapered end 40 which conforms to the shape of tapered tip 36, as illustrated in FIG. 2. Located within housing 38 is a sample tube 42. Sample tube 42 ultimately receives the sample once the operating rod 32 is retracted. Operating rod 32 is movable within cavity 44. Housing 38 forms a second cavity 46, which also circumscribes the operating rod 32. Within cavity 46 are latches 48. In the preferred embodiment, one or more latches 48 may be used without departing from the spirit of the invention. As seen in FIGS. 3 and 4, a first position is defined as any rod position wherein latches 48 are not engaged in the groove 34 and the rod 32 moves independently of the housing 38 and a second position is defined by the latches 48 engage the groove 34. In the preferred embodiment, the latches 48 have an L-shape which includes a lower surface 50, which is supported by surface 52. Surface 52 is one of the defining walls for cavity 46. A cap 54 is secured to housing 38 to loosely retain the latches 48 within cavity 46. As seen in FIGS. 5a and 5b, latches 48 are biased radially inwardly by a circular spring 56, which is located in groove 58. As can readily be seen by looking at FIGS. 3–5, when the sampler housing 38 is inserted into the area where the sample is to be obtained, the operating rod 32, which is connected through thread 60 to a drill rod not shown, is retracted. Tapered tip 36 then is retracted into bore 44 while, at the same time, groove 34 advances towards latches 48.

As previously stated, latches 48 have a longitudinal segment 62 which is disposed generally parallel to operating rod 32. Latches 48 also have a transverse segment 64 which is disposed transverse to longitudinal segment 62, hence defining the L-shaped nature of latches 48 in the preferred embodiment. Preferably, transverse segment 64 is substantially thicker than longitudinal segment 62. The transverse segment is formed having a first surface facing said rod conforming circumferentially to the shape of the operating rod 32 to allow the operating rod 32 to move bi-directionally. The first surface is biased against said operating rod 32 until the first surface becomes aligned with the annular groove 34 to engage the annular groove 34. The transverse segment 64 extends from said longitudinal segment 62 and toward the operating rod 32 and has the circumferential conforming surface on one end thereof; the longitudinal segment 62 has a circumferential shape substantially conforming to the annular groove 34 in the operating rod 32. In the preferred embodiment, transverse segment 64 has a surface 51 opposing the rod 32 as seen on FIG. 1. Surface 51 as seen in FIG. 6 A–D, circumferentially conforms to the shape of rod 32. Upon sufficient retraction of operating rod 32, as seen by comparing FIGS. 3 and 4, the transverse segments 64 come into alignment with groove 34. At that time, circular spring 56, which has been removed for clarity from FIGS. 3 and 4 but shown in detail in FIGS. 5a and b, urges the latches 48 radially inwardly so that they move into groove 34. At that point, the operating rod 32 is firmly latched to the housing 38. Thereafter, the housing 38 is advanced and the soil sample is advanced into cavity 44 and then to sample tube 42. Thereafter, the housing 38 is simply extracted from the sample area and the sample is retained within sample tube 42. In order to reuse the apparatus A of the present invention, the operating rod 32 has to be released from latches 48. Cover 54 is removed. A releasing tool 49 (see FIGS. 6A and 6B) is inserted over rod 32. The tool effectively spreads the latches 48 outwardly against the bias of circular spring 56 until the operating rod 32 can be manually pushed downwardly to reassume its position shown in FIG. 2. At that time, the apparatus A is ready for reuse after cap 54 is replaced. The releasing tool can have any one of a number of designs which allow it to be inserted over rod 32 and operated so as to spread the latches 48 to get them out of groove 34.

Different means of radially biasing the latches 48 inwardly can be used without departing from the spirit of the invention.

The apparatus A of the present invention offers many advantages over the sampler of the prior art as illustrated in FIG. 1. The apparatus A may be used in any orientation. The apparatus A allows smooth movement of the operating rod 32 as it is being retracted. This movement is illustrated by comparing FIG. 3 to FIG. 4. Even if during the retraction motion there is a brief movement in the opposite direction, the result is that there is no effect on the smooth operation of the operating rod 32. Unlike the prior art illustrated in FIG. 1, jamming does not occur because of the latching balls 24 jamming up against tapered surface 30. Instead, the point loads transmitted through the latching balls 24 at the point of contact with tapered surface 30, the apparatus A of the present invention distributes the loads in the latching procedure illustrated in FIG. 4. The housing 38 is constructed in a manner to support the latches 48. The circular spring 56 smoothly urges the latches 48 into groove 34. The force exerted is preferably only in a transverse plane to the plane of the longitudinal axis of rod 32. This feature promotes use of the apparatus A in any orientation since there is no reliance on gravity to accomplish the latching procedure. Having a leading surface conforming to the shape of rod 32 facilitates bi-directional movement of rod 32 which can occur during normal operation until groove 34 becomes aligned with longitudinal segment 62. Due to the shape of transverse segment 64, the stresses are distributed from the contact between transverse segment 64 and groove 34. Groove 34 can be continuous around rod 32 or in segments. The overall profile of the apparatus A can be same as that of the prior art illustrated in FIG. 1, yet it contains numerous advantages in sampling, particularly where the sample is taken horizontally, such as under a roadway, a tank, or an edifice. In view of the heightened interest in taking soil samples to determine the extent of contamination and the effectiveness of remediation, the apparatus A of the present invention is of tremendous assistance to engineers and technicians whose responsibilities are to obtain sufficient samples of an affected zone to make scientific determinations as to contamination or clean-up of the area. The sampler can be used in other applications for taking samples of ground water and can also be adapted for subsurface use in oil or gas exploration and production operations.

The foregoing disclosure and description of the invention are illustrative and explanatory thereof, and various changes in the size, shape and materials, as well as in the details of the illustrated construction, may be made without departing from the spirit of the invention.

What is claimed is:

1. A soil sampler, comprising:

a housing;

a rod movably mounted with respect to said housing between a first position extending beyond said housing to assist in penetrating the housing into the soil, and a second position where said rod is retracted within said housing to allow a sample to enter said housing upon advancement of said housing into the soil;

an annular groove on said rod; and latch means having a longitudinal segment disposed generally parallel to said rod, the longitudinal segment having a transverse segment extending from the longitudinal segment, said latch means in said housing adjacent to said rod, said latch means movable between a first latch position with respect to said rod wherein said rod can be moved with respect to said housing from said rod's first position to said rod's second position, and a second latch position of said latch means with respect to said rod, wherein said transverse segment of said latch means being biased radially inward by a biasing means for extending said transverse segment of said latch means into said annular groove for holding said rod stationary with respect to said housing, whereupon a force applied to said rod, when latched in said rod's second position, is transmitted to said housing to advance said housing into the soil to collect the sample;

wherein said transverse segment of said latch means includes a first curved surface facing and surrounding said rod and conforming circumferentially to the shape of said annular groove.

2. The sampler of claim 1, wherein:

said biasing means in said housing acts on said latch means to bias said latch means toward said rod.

3. The sampler of claim 2, wherein:

said latch means is biased into contact with said rod, said contact permitting bi-directional movement of said rod with respect to said housing until said annular groove is aligned with said latch means.

4. The sampler of claim 3, wherein: said first surface of said transverse segment facing said rod allows said rod to move bi-directionally with said first surface biased against said rod until said first surface becomes aligned with said annular groove to engage said annular groove.

5. The sampler of claim 4, wherein:

said latch means comprises at least one latch formed having a biasing groove therein;

said biasing means disposed in said biasing groove and around said rod to urge said latch toward said rod.

6. The sampler of claim 5, wherein:

said transverse segment extending from said longitudinal segment and toward said rod and having said circumferential conforming surface on one end thereof; and said longitudinal segment having a circumferential shape substantially conforming to said annular groove in said rod.

7. The sampler of claim 6, wherein:

said biasing groove is disposed on said longitudinal segment opposite said conforming surface on said transverse segment.

8. The sampler of claim 7, wherein:

said transverse segment is disposed at one end of said longitudinal segment;

said housing formed having an internal shoulder to support said latch; and said transverse segment and said longitudinal segment are held against said rod by a circular spring disposed in said biasing groove.

9. The sampler of claim 8, further comprising:

a sample tube in said housing surrounding said rod;

said housing and rod having a conforming pointed leading edge when said rod is disposed within said sample tube;

whereupon retraction of said rod allows said latch segments to enter said groove in said rod, said sample tube is exposed to allow sampling by advancing said housing.

10. The sampler of claim 2, wherein said said biasing means in said housing acts on said latch means for biasing said latch means against said rod in a manner as to allow latching of said rod to said housing in any orientation of said housing.

11. The sampler of claim 10, wherein:

said biasing means exerts solely a radially inward force on said latch means in a plane transverse to the longitudinal axis of said rod.

12. The sampler of claim 1, wherein said latch means has a variable circumferential radius.

13. A soil sampler, comprising:

a housing;

a rod movably mounted with respect to said housing between a first position extending beyond said housing to assist in penetrating the housing into the soil, and a second position where said rod is retracted within said housing to allow a sample to enter said housing upon advancement of said housing into the soil;

an annular groove on said rod;

latch means having a longitudinal segment disposed generally parallel to said rod and a transverse segment extending from the longitudinal segment, said latch means in said housing adjacent to said rod, said latch means movable between a first latch position with respect to said rod wherein said rod can be moved with respect to said housing from said rod's first position to said rod's second position, and a second latch position of said latch means with respect to said rod, wherein said transverse segment of said latch means being biased radially inward by a biasing means for extending said transverse segment of said latch means into said annular groove for holding said rod stationary with respect to said housing, whereupon a force applied to said rod, when latched in said rod's second position, is transmitted to said housing to advance said housing into the soil to collect the sample;

wherein said transverse segment of said latch means includes a first curved surface facing and surrounding said rod, and conforming circumferentially to the shape of said annular groove;

wherein said biasing means in said housing acts on said latch means to bias said latch means toward said rod;

wherein said biasing means in said housing acts on said latch means for biasing said latch means against said rod in a manner as to allow latching of said rod to said housing in any orientation of said housing; and wherein said biasing means exerts solely a radially inward force on said latch means in a plane transverse to the longitudinal axis of said rod; and a release tool insertable over said rod to spread said latch means away from said rod and out of said annular groove in said rod to facilitate resetting said rod from said rod's second position to said rod's first position.

* * * * *